(12) United States Patent
Du et al.

(10) Patent No.: US 11,298,459 B2
(45) Date of Patent: Apr. 12, 2022

(54) WEARABLE MEDICAL DEVICE FOR MONITORING INTRAVENOUS INJECTION

(71) Applicant: International Business Machines Corporation, Armonk, NY (US)

(72) Inventors: Jing Du, Beijing (CN); Tzu-Chen Chao, Taipei (TW); Ci-Wei Lan, Keelung (TW); Xiang Yu Yang, Xi'an (CN); Chao Zhang, Beijing (CN); Xin Fang Hao, Beijing (CN)

(73) Assignee: International Business Machines Corporation, Armonk, NY (US)

( * ) Notice: Subject to any disclaimer, the term of this patent is extended or adjusted under 35 U.S.C. 154(b) by 598 days.

(21) Appl. No.: 16/027,425

(22) Filed: Jul. 5, 2018

(65) Prior Publication Data

US 2020/0009321 A1 Jan. 9, 2020

(51) Int. Cl.
*A61M 5/00* (2006.01)
*A61M 5/172* (2006.01)
(Continued)

(52) U.S. Cl.
CPC ...... *A61M 5/1723* (2013.01); *A61M 5/16877* (2013.01); *G16H 20/17* (2018.01);
(Continued)

(58) Field of Classification Search
CPC ............ A61M 5/1723; A61M 5/16877; A61M 5/14244; A61M 2205/3303; A61M 2205/3334; A61M 2205/3584; A61M 2205/50; A61M 2205/502; A61M 2205/52; A61M 2205/3553; A61M 2205/33;
(Continued)

(56) References Cited

U.S. PATENT DOCUMENTS 3,512,748 A * 5/1970 Wilson ................ A61M 39/283
251/8
(Continued)

FOREIGN PATENT DOCUMENTS

WO 2012058192 A1 5/2012
WO 2016038498 A1 3/2016

OTHER PUBLICATIONS

McLean, T., "West's Smartdose Platform: A Wearable Engineered With Both Patient & Pharma Partner in Mind", West, © 2016 Frederick Furness Publishing Ltd, 5 pages, <https://www.ondrugdelivery.com/publications/70/West.pdf>.

*Primary Examiner* — Nathan R Price
*Assistant Examiner* — Tania Ismail
(74) *Attorney, Agent, or Firm* — Stosch Sabo

(57) ABSTRACT

A wearable medical device comprising an annular housing configured to attach to a wrist of a patient. The wearable medical device having a first receptacle attached to the annular housing for receiving a first portion of a tube of an intravenous delivery system. The wearable medical device comprising a flow regulator attached to the annular housing and in contact with the first portion of the tube, where the flow regulator is configured to modify a geometric characteristic of the first portion of the tube. The wearable medical device further comprising a wireless transmitter for communicating with a user console.

13 Claims, 7 Drawing Sheets

(51) Int. Cl.
*A61M 5/168* (2006.01)
*G16H 20/17* (2018.01)
*A61M 5/142* (2006.01)

(52) U.S. Cl.
CPC ..... *A61M 5/14244* (2013.01); *A61M 2205/18* (2013.01); *A61M 2205/33* (2013.01); *A61M 2205/3303* (2013.01); *A61M 2205/3331* (2013.01); *A61M 2205/3334* (2013.01); *A61M 2205/3379* (2013.01); *A61M 2205/3389* (2013.01); *A61M 2205/3553* (2013.01); *A61M 2205/3569* (2013.01); *A61M 2205/3576* (2013.01); *A61M 2205/3584* (2013.01); *A61M 2205/50* (2013.01); *A61M 2205/502* (2013.01); *A61M 2205/52* (2013.01); *A61M 2230/30* (2013.01)

(58) Field of Classification Search
CPC .. A61M 2205/3576; A61M 2205/3331; A61M 2205/3379; G06F 19/3468; G06F 19/363
See application file for complete search history.

(56) References Cited

U.S. PATENT DOCUMENTS

| | | | |
|---|---|---|---|
| 8,915,399 B1* | 12/2014 | Nystrom | A61K 49/0002 222/63 |
| 9,067,051 B2* | 6/2015 | Loth | A61M 39/284 |
| 9,844,631 B2 | 12/2017 | Bureau | |
| 2010/0069848 A1* | 3/2010 | Alferness | A61M 5/14248 604/151 |
| 2013/0204227 A1* | 8/2013 | Bochenko | A61M 5/31 604/506 |
| 2016/0122701 A1* | 5/2016 | Higgs, III | C12M 35/04 435/257.1 |
| 2016/0256106 A1 | 9/2016 | Krasnow et al. | |
| 2016/0256665 A1* | 9/2016 | Ahn | |
| 2016/0350512 A1* | 12/2016 | Jedwab | G16H 20/17 |
| 2017/0182242 A1 | 6/2017 | Galitz et al. | |

\* cited by examiner

WEARABLE MEDICAL DEVICE FOR MONITORING INTRAVENOUS INJECTION

BACKGROUND

The present disclosure relates to medical devices, and, more specifically, to medical devices for regulating intravenous injections.

SUMMARY

Aspects of the present disclosure are directed toward a computer-implemented method comprising establishing, by a wearable medical device, wireless communication between the wearable medical device, an intravenous delivery system, a user console, and a plurality of biometric sensors. The plurality of biometric sensors can be configured to measure biometric characteristics of a patient. The method can further comprise receiving authorization, at the wearable medical device and from the user console, for a medication to be delivered intravenously via the intravenous delivery system to the patient. The medication can be associated with a drug type, a volume, and a flow rate. The method can further comprise metering, by the wearable medical device, the volume of the medication to the intravenous delivery system at the flow rate. The metering the volume at the flow rate can comprise modifying, by the wearable medical device, a geometric characteristic of a tube of the intravenous delivery system. The method can further comprise sending, by the wearable medical device and to the user console, an indication that the medication is delivered to the patient in response to metering the volume of the medication to the intravenous delivery system.

Further aspects of the present disclosure are directed to a wearable medical device comprising an annular housing configured to attach to a wrist of a patient, a first receptacle attached to the annular housing for receiving a first portion of a tube of an intravenous delivery system, and a flow regulator attached to the annular housing and in contact with the first portion of the tube. The flow regulator can be configured to modify a geometric characteristic of the first portion of the tube. The wearable medical device can further comprise a pulse monitor attached to the annular housing and configured to contact the wrist of the patient and measure a pulse of the patient. The wearable medical device can further comprise a wireless transmitter for communicating with a user console.

Further aspects of the present disclosure are directed toward a computer program product comprising a computer readable storage medium having program instructions embodied therewith. The program instructions executable by a processor to cause the processor to perform a method comprising establishing wireless communication between a wearable medical device, an intravenous delivery system, a user console, and a plurality of biometric sensors. The plurality of biometric sensors can be configured to measure biometric characteristics of a patient. The method can further comprise receiving authorization, from the user console, for a medication to be delivered intravenously via the intravenous delivery system to the patient. The medication can be associated with a drug type, a volume, and a flow rate. The method can further comprise metering the volume of the medication to the intravenous delivery system at the flow rate. Metering the volume at the flow rate can comprise modifying a geometric characteristic of a tube of the intravenous delivery system. The method can further comprise sending, to the user console, an indication that the medication is delivered to the patient in response to metering the volume of the medication to the intravenous delivery system.

The above summary is not intended to represent each embodiment of, every aspect of, and/or each implementation of, the present disclosure.

BRIEF DESCRIPTION OF THE DRAWINGS

The drawings included in the present application are incorporated into, and form part of, the specification. They illustrate embodiments of the present disclosure and, along with the description, serve to explain the principles of the disclosure. The drawings are only illustrative of certain embodiments and do not limit the disclosure.

Figure 1:
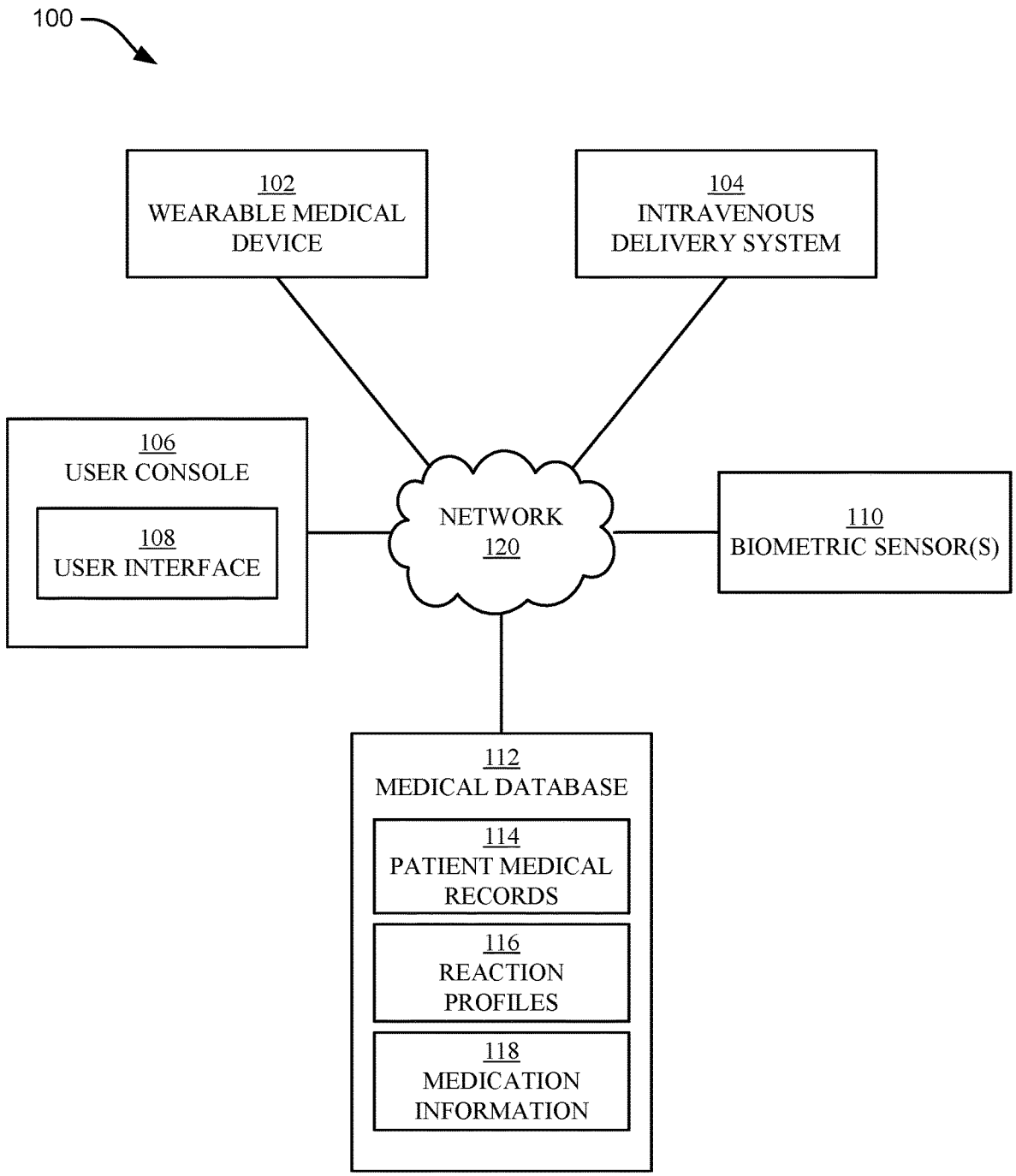
FIG. 1 illustrates a block diagram of an example medical network, in accordance with some embodiments of the present disclosure.

While the present disclosure is amenable to various modifications and alternative forms, specifics thereof have been shown by way of example in the drawings and will be described in detail. It should be understood, however, that the intention is not to limit the present disclosure to the particular embodiments described. On the contrary, the intention is to cover all modifications, equivalents, and alternatives falling within the spirit and scope of the present disclosure.

DETAILED DESCRIPTION

Aspects of the present disclosure are directed toward medical devices. More particular aspects of the present disclosure are directed toward wearable medical devices for regulating intravenous injections. While not limited to such applications, aspects of the present disclosure can be more appropriately understood using this context.

Intravenous injections are a therapeutic method for delivering medication to patients. Intravenous injections can be useful for quickly administering medication to a patient via the patient's circulatory system. Intravenous injections can be delivered by an intravenous delivery system. Intravenous delivery systems can include, but are not limited to, a sterile container storing a medication (e.g., glass bottle, plastic bottle, plastic bag, etc.), a sterile tube (e.g., a plastic tube) having a predefined diameter (e.g., 3 mm, 4 mm, etc.), and a hypodermic needle (e.g., 12-gauge, 14-gauge, 16-gauge, 18-gauge, 20-gauge, 22-gauge, 24-gauge, 26-gauge, etc.).

The hypodermic needle can be inserted into a patient's vein. In some embodiments, intravenous injections are administered by a healthcare practitioner using a needle and a syringe storing the appropriate volume of medication. Intravenous delivery systems can utilize various methods to control medication flow rates such as drip chambers, infusion pumps, pressure bags, and manually applied pressure (e.g., when administered by a healthcare practitioner using a syringe).

Delivering medications intravenously can be associated with numerous challenges. For example, the medication flow rate and the medication volume can be difficult to control and/or are susceptible to human error. A healthcare practitioner administering a medication by syringe has limited ability to precisely regulate the flow rate. As another example, a healthcare practitioner can inadvertently administer an incorrect volume of medication.

Aspects of the present disclosure overcome the aforementioned challenges and are directed toward a wearable medical device for verifying intravenous medication information, regulating the flow rate of the medication by modifying a geometry of the infusion tube, and monitoring patient health before, during, and after delivery of the medication. Aspects of the present disclosure realize numerous advantages and improvements.

First, aspects of the present disclosure increase flow rate precision relative to manual injections (e.g., using a syringe) or gravity-based injections. Aspects of the present disclosure can regulate a flow rate of the medication by altering a geometry of the infusion tube. The altered geometry can directly (e.g., altered cross-section) or indirectly (e.g., altered fluid viscosity) regulate flow rate. Thus, aspects of the present disclosure provide improved flow rate precision when performing intravenous injections.

Second, aspects of the present disclosure improve usability relative to other intravenous delivery systems. For example, aspects of the present disclosure are attachable to any infusion delivery system utilizing a flexible tube. Thus, aspects of the present disclosure can be utilized with minimal equipment changes, limited re-training, and low capital cost.

Third, aspects of the present disclosure can detect adverse reactions (e.g., allergic reactions) before the adverse reaction becomes visible. As opposed to traditional settings relying on a healthcare practitioner to detect adverse reactions, aspects of the present disclosure advantageously monitor biometric characteristics of the patient using a plurality of sensors before, during, and after the infusion. Thus, aspects of the present disclosure improve detection of adverse reactions and improve patient safety.

The aforementioned advantages are example advantages and not all advantages are necessarily discussed. Furthermore, embodiments of the present disclosure exist that can contain all, some, or none of the aforementioned advantages while remaining within the spirit and scope of the present disclosure.

Referring now to the drawings, FIG. 1 illustrates a block diagram of an example medical network 100, in accordance with some embodiments of the present disclosure. Medical network 100 can include a wearable medical device 102, an intravenous delivery system 104, a user console 106, one or more biometric sensors 110, and a medical database 112. The aforementioned components can be connected by a network 120. Network 120 can be, but is not limited to, a physical network (e.g., Ethernet, Infiniband, etc.), a wireless network (e.g., cellular network, wireless local area network (WLAN), wireless sensor network, satellite communication network, microwave network, etc.), a personal area network (e.g., Bluetooth network, near-field communication (NFC) network, etc.), or a combination of the aforementioned networks.

Wearable medical device 102 can comprise a medical device configured to be worn on a patient's wrist for regulating intravenous injections, verifying medication information, and monitoring patient health for adverse reactions. Wearable medical device 102 is discussed in more detail hereinafter with respect to FIG. 2.

Intravenous delivery system 104 can comprise any system configured to intravenously deliver medication to a patient (e.g., syringes, drip chambers, pressure bags, infusion pumps, etc.). In some embodiments, intravenous delivery system 104 comprises a container storing a medication, a hypodermic needle configured to be inserted into a patient's vein, and a flexible tube connecting the container to the hypodermic needle.

User console 106 can comprise user interface 108. A healthcare practitioner can use user interface 108 to select dosage information (e.g., a medication, a volume of the medication, a flow rate of the volume of the medication, etc.) and authorize administration of the medication.

Biometric sensors 110 can be, but are not limited to, pulse rate sensors, temperature sensors, blood pressure sensors, blood sugar sensors, visual sensors (e.g., detecting pupil dilation, perspiration, gesticulation, etc.), acoustic sensors (e.g., detecting sounds such as retching, coughing, moaning, verbal requests, etc.), and/or other sensors. Although biometric sensors 110 are shown separately, in some embodiments, one or more of the biometric sensors 110 are physically connected to wearable medical device 102.

Medical database 112 can comprise patient medical records 114, reaction profiles 116, and medication information 118. Patient medical records 114 can comprise electronic health records (EHRs), electronic medical records (EMRs), or different records storing personal and medical information about a patient.

Reaction profiles 116 can comprise rules defining an adverse reaction to a medication and/or a patient emergency. Reaction profiles 116 can use rules defined according to respective types of biometric data collected from biometric sensors 110. For example, a first reaction profile could be associated with a pulse rate above a first threshold and a systolic blood pressure below a second threshold (e.g., indicating anaphylaxis).

Medication information 118 can comprise recommended dosages, flow rates, and other information for particular medications. In some embodiments, patient medical records 114, reaction profiles 116, and/or medication information 118 are interrelated in a many-to-many database. For example, a first patient medical record in patient medical records 114 can point to numerous medications in medication information 118 indicating the patient is using those medications. Furthermore, individual medications in medication information 118 can point to numerous reaction profiles in reaction profiles 116 that indicate various types of adverse reactions associated with individual medications (e.g., allergic reaction, heart attack, stroke, shock, shortness of breath, etc.).

In some embodiments of the present disclosure, wearable medical device 102 can be affixed to a flexible tube of an intravenous delivery system 104 and establish networked communication (e.g., a personal area network) with at least user console 106. In some embodiments, wearable medical device 102 also establishes communication with intravenous delivery system 104, biometric sensors 110, and/or medical database 112. Wearable medical device 102 can receive dosage information based on user input to user interface 108 of user console 106. Wearable medical device 102 can verify that the dosage information input to user console 106 is consistent with dosage information in medication information 118. Wearable medical device 102 can verify that the patient medical record 114 associated with the dosage information is the same patient as is wearing the wearable medical device 102 using patient medical records 114. Wearable medical device 102 can administer the medication at the determined flow rate and for the determined volume contained in the dosage information by modifying the geometry of the flexible tube of the intravenous delivery system 104. The wearable medical device 102 can monitor the biometric sensors 110 and compare the collected data to reaction profiles 116 to identify any adverse reaction that the patient experiences as a result of the administered medication. After administering the medication, the wearable medical device 102 can notify the user console 106 and/or update the patient medical record 114 indicating the completion of the intravenous injection. In the event that the wearable medical device 102 detects an adverse reaction as a result of comparing the collected data from the biometric sensors 110 to the reaction profiles 116, the wearable medical device 102 can stop delivery of the medication and/or notify the user console 106 (or a different device) of the detected adverse reaction.

FIG. 1 is intended to illustrate the major components of an example medical network 100. However, in some embodiments, medical network 100 can exhibit more or fewer components than the components shown. In some embodiments, the components illustrated in medical network 100 can have greater or lesser complexity than shown, and they can exist, if they exist at all, in alternative configurations.

Figure 2:
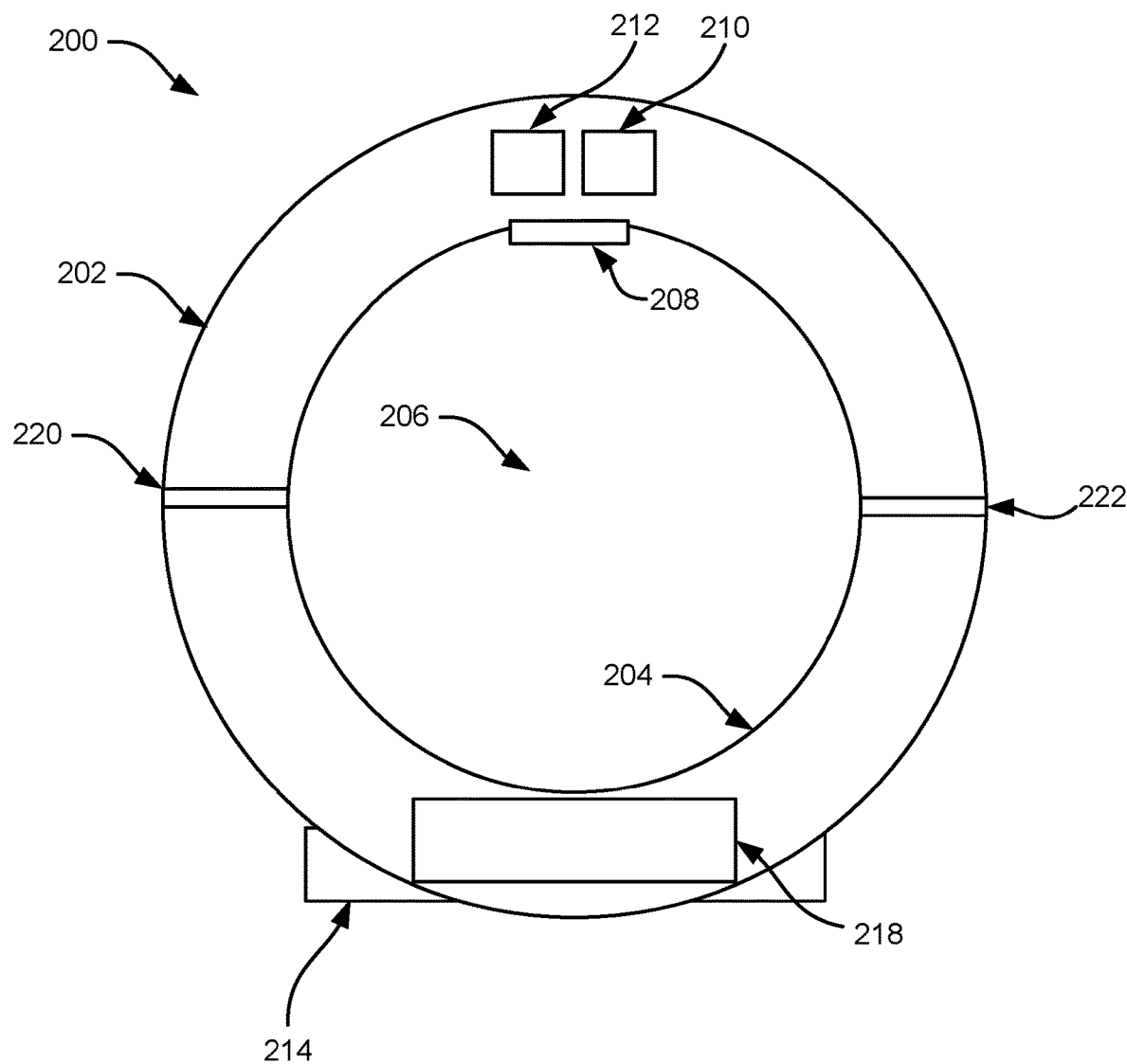
FIG. 2 illustrates a block diagram of an example wearable medical device, in accordance with some embodiments of the present disclosure.

Referring now to FIG. 2, illustrated is a top view of an example wearable medical device 200, in accordance with some embodiments of the present disclosure. In some embodiments, wearable medical device 200 is consistent with wearable medical device 102 of FIG. 1.

Wearable medical device 200 can comprise an annular housing having an outer portion 202, an inner portion 204, and an opening 206. Opening 206 can be configured to fit over a patient's wrist. In some embodiments, opening 206 can comprise a diameter, a length, or a width having a dimension between two inches and six inches. In some embodiments, the opening 206 is associated with a dimension between three inches and four inches.

In some embodiments, the annular housing comprises a plastic (e.g., thermoplastic, thermoset, etc.), an elastomer, a metal (e.g., stainless steel, titanium, alloy, etc.), a ceramic, or a different material, or combination of materials. In some embodiments, the annular housing comprises a composite material having a matrix material (e.g., a polymer, a ceramic, a metal, etc.), a reinforcement material (e.g., glass, carbon, aramid, etc.), a reinforcement type (e.g., long-fiber, short-fiber, continuous-fiber, etc.), and a reinforcement mass loading factor (e.g., 20%, 30%, 40%, 50%, or a different percentage reinforcement by mass).

In some embodiments, the annular housing is fabricated by molding (e.g., injection-molding, transfer-molding, compression-molding, rotational molding, overmolding, insert molding, etc.), filament-winding, infusing (e.g., vacuum assisted resin transfer molding (VARTM), resin transfer molding (RTM), etc.), casting, machining, or a different fabrication technique, or combination of fabrication techniques.

Wearable medical device 200 can further comprise at least one biometric sensor 208. In some embodiments, biometric sensor 208 comprises a pulse monitor configured to reside on the inner portion 204 and contact a patient's wrist. In other embodiments, biometric sensor 208 can comprise a temperature sensor, a perspiration sensor, a blood pressure sensor (e.g., in embodiments where the inner portion 204 functions as a blood pressure cuff), or other sensors.

Wearable medical device 200 can further comprise a control unit 210 configured to store and execute computer-readable instructions. In some embodiments, control unit 210 comprises a processor and a non-transitory memory. In some embodiments, control unit 210 establishes network communication with other devices (e.g., intravenous delivery system 104, user console 106, biometric sensors 110, and/or medical database 112 of FIG. 1) using communication unit 212. In some embodiments, control unit 210 regulates a flow rate and a volume of a medication by actuating flow regulator 218 to modify a geometry of a tube located in tubing receptacle 214.

Wearable medical device 200 can further comprise the communication unit 212. Communication unit 212 can be configured to communicate with one or more devices using NFC, Bluetooth, or a different wired or wireless communication technique. Communication unit 212 can comprise a wireless transmitter, a transceiver, or a different communication device.

Wearable medical device 200 can further comprise the tubing receptacle 214 for receiving a portion of a tube of an intravenous delivery system (e.g., intravenous delivery system 104 of FIG. 1). Tubing receptacle 214 can comprise, but is not limited to, a clamping mechanism, a push-fit mechanism, or a different mechanism or combination of mechanisms configured to receive a flexible tube of an intravenous delivery system. In some embodiments, tubing receptacle 214 comprises a push-fit channel mechanism having a channel diameter equal to or larger than a diameter of the tube and a channel opening width less than the diameter of the tube.

Wearable medical device 200 can further comprise the flow regulator 218 for regulating the flow rate (e.g., volumetric flow rate, mass flow rate, flow velocity, etc.) and dosage volume while administering a medication intravenously. Flow regulator 218 can regulate flow by numerous techniques such as, but not limited to, altering a curvature of the tube and altering a cross-sectional area of the tube. In some embodiments, flow regulator 218 alters a curvature or a cross-sectional area of the tube by actuating a clamp, compressing a spring, activating a shape-memory polymer, articulating a valve, or a different flow-regulation mechanism, or a combination of flow regulation mechanisms. Flow regulator 218 can alter a medication flow rate directly (e.g., by modifying a cross-sectional area of the tube) and/or indirectly (e.g., by altering the shear stress experienced by non-Newtonian medications, the altered shear stress causing altered viscosity).

In some embodiments, wearable medical device 200 can further comprise fasteners 220 and 222. Although two fasteners 220, 222 are shown, in some embodiments, more or fewer fasteners are used, if they are used at all (e.g., no fasteners can be used in embodiments where the annular housing comprises a material of sufficient flexibility to expand over, and fit to, a patient's wrist). Fasteners 220, 222 can be elastomeric fasteners (e.g., flex-fit fasteners), mechanical fasteners (e.g., latches, clips, clasps, push-fit fasteners, friction-based fasteners, etc.), magnetic fasteners, or different fasteners.

In embodiments where fasteners 220, 222 are elastomeric fasteners, the fasteners 220, 222 can comprise polyisoprene (natural or synthetic), polybutadiene, chloroprene, butyl rubber, halogenated butyl rubbers, styrene-butadiene, nitrile rubber (NBR), hydrogenated nitrile rubber (HNBR), ethylene propylene rubber (EPM), ethylene propylene diene rubber (EPDM), epichlorohydrin rubber (ECO), polyacrylic rubber (ACM), silicone rubber, fluorosilicone rubber, fluoroelastomer, perfluoroelastomer, thermoplastic elastomer (TPE), elastolefin, or a different elastomer.

In embodiments where the fasteners 220, 222 are elastomers, the elastomers can exhibit properties appropriate for expanding over a hand of a patient and fitting to a patient's wrist. For example, the elastomers can exhibit an elastic modulus (e.g., Young's modulus) of between 0.05 gigapascals (GPa) and 2.0 GPa. In some embodiments, the elastomers exhibit an elastic modulus of less than 1.0 GPa.

In embodiments where fasteners 220, 222 are mechanical fasteners, fastener 220 can be a hinge and fastener 222 can be a latch, clip, clasp, push-fit fastener, friction-based fastener, or a different mechanical fastener (or vice versa).

In embodiments where fasteners 220, 222 are magnetic fasteners, fastener 220 can be a hinge and fastener 222 can comprise two magnets having opposite polarities (or vice versa).

Fasteners 220, 222, biometric sensor 208, control unit 210, communication unit 212, tubing receptacle 214, and flow regulator 218 can be contemporaneously fabricated with, or subsequently assembled to, the wearable medical device 200. In embodiments utilizing contemporaneous fabrication, fasteners 220, 222, biometric sensor 208, control unit 210, communication unit 212, tubing receptacle 214, and/or flow regulator 218 can be contemporaneously fabricated to wearable medical device 200 by, for example, insert molding, over-molding, or a different technique. In such embodiments, the fasteners 220, 222, biometric sensor 208, control unit 210, communication unit 212, tubing receptacle 214, and/or flow regulator 218 can be placed in a mold cavity and the mold cavity subsequently filled with material, thus attaching the fasteners 220, 222, biometric sensor 208, control unit 210, communication unit 212, tubing receptacle 214, and/or flow regulator 218 to the wearable medical device 200 at approximately the same time as material forming the annular housing (e.g., outer portion 202, inner portion 204) cools, cures, or otherwise solidifies.

In embodiments utilizing post-fabrication assembly, fasteners 220, 222, biometric sensor 208, control unit 210, communication unit 212, tubing receptacle 214, and/or flow regulator 218 can be subsequently attached to wearable medical device 200 by mechanical fastening, adhesive bonding, welding, ultrasonic welding, or a different assembly technique. In some embodiments, a combination of contemporaneous fabrication and post-fabrication assembly is used for different components of wearable medical device 200.

FIG. 2 is intended to illustrate the major components of an example wearable medical device 200. However, in some embodiments, wearable medical device 200 can exhibit more or fewer components than the components shown. In some embodiments, the components illustrated in wearable medical device 200 can have greater or lesser complexity than shown, and they can exist, if they exist at all, in alternative configurations.

Figure 3:
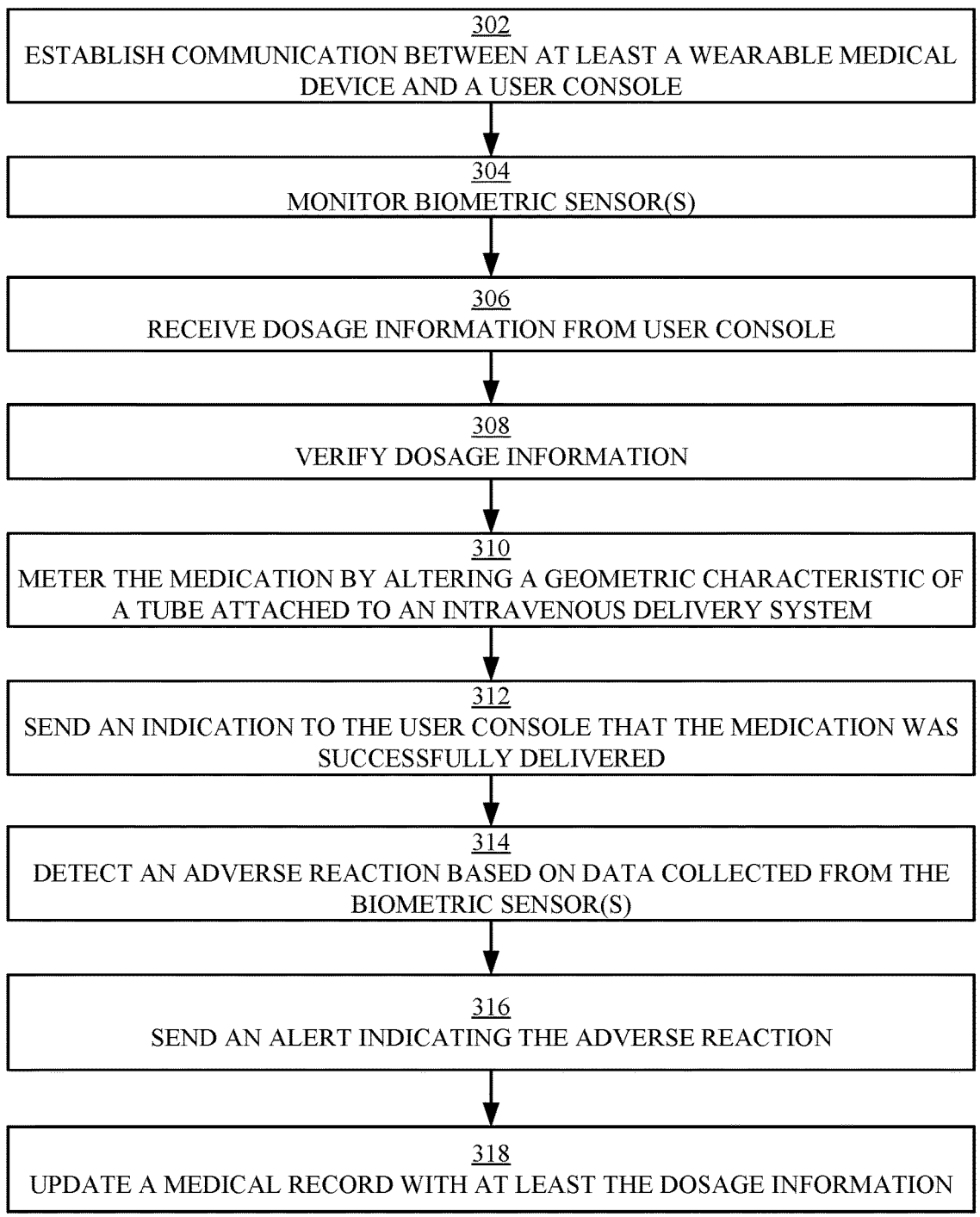
FIG. 3 illustrates a flowchart of an example method for regulating an intravenous injection using a wearable medical device, in accordance with some embodiments of the present disclosure.

Referring now to FIG. 3, illustrated is a flowchart of an example method for administering an intravenous medication using a wearable medical device, in accordance with some embodiments of the present disclosure. The method 300 can be implemented by a wearable medical device (e.g., wearable medical device 102 of FIG. 1, wearable medical device 200 of FIG. 2, or wearable medical device control unit 700 of FIG. 7). For clarity, the method 300 will be described as being executed by a wearable medical device control unit, however, the method 300 can also be implemented by alternative configurations of hardware and/or software.

In operation 302, the wearable medical device control unit can establish communication between at least a wearable medical device (e.g., wearable medical device 102 of FIG. 1 and/or wearable medical device 200 of FIG. 2) and a user console (e.g., user console 106 of FIG. 1). In some embodiments, the wearable medical device control unit also establishes communication with an intravenous delivery system (e.g., intravenous delivery system 104 of FIG. 1), one or more biometric sensors (e.g., biometric sensors 110 of FIG. 1, biometric sensor 208 of FIG. 2), and/or a medical database (e.g., medical database 112 of FIG. 1).

In operation 304, the wearable medical device control unit can monitor data collected from one or more biometric sensors (e.g., biometric sensors 110 of FIG. 1 and/or biometric sensor 208 of FIG. 2). The biometric sensors can collect data from a patient, and the wearable medical device control unit can use the collected data to develop baseline (e.g., typical, common, historical, etc.) vital signs for the patient.

In operation 306, the wearable medical device control unit can receive authorization from the user console (e.g., based on user input received at a user interface of the user console) to deliver a medication according to dosage information to a patient via an intravenous delivery system. In some embodiments, the dosage information comprises a patient identifier, a medication, a volume of the medication, a delivery flow rate of the volume of the medication, and/or credentials of the healthcare practitioner prescribing the medication.

In operation 308, the wearable medical device control unit can verify the dosage information. In some embodiments, verifying the dosage information comprises verifying the patient, verifying the volume and flow rate, reviewing adverse medication interactions/reactions, and verifying the credentials of the healthcare practitioner prescribing the medication. Operation 308 is discussed in more detail hereinafter with respect to FIG. 6.

In operation 310, the wearable medical device control unit can meter the volume of the medication at the delivery flow rate by altering a geometric characteristic of a tube containing the medication. In some embodiments, altering a geometric characteristic of the tube comprises altering a curvature of the tube and/or altering a cross-sectional area of the tube. Operation 310 is discussed in more detail hereinafter with respect to FIG. 4.

In operation 312, the wearable medical device control unit can send an indication to the user console that the medication was successfully delivered. In some embodiments, the indication can comprise a notification presented on a user interface, a short message service (SMS) notification sent to a mobile device of the healthcare practitioner, or a different indication.

In operation 314, the wearable medical device control unit can detect an adverse reaction based on updated data collected from the biometric sensors. In some embodiments, operation 314 detects an adverse medical condition by matching a set of updated biometric data collected from a patient to a set of rules in a medical database (e.g., medical database 112 of FIG. 1) that indicate an adverse reaction. Operation 314 is discussed in more detail hereinafter with respect to FIG. 5.

In operation 316, the wearable medical device control unit can send an alert (e.g., a notification, a text massage, an email, a voice message, an acoustic alarm, etc.) indicating the adverse reaction. In some embodiments, the alert can be sent to the user console, to a mobile device associated with the healthcare practitioner (e.g., a tablet, a pager, a mobile phone, etc.), to an emergency management system, or to a different device.

In operation 318, the wearable medical device control unit can update an electronic medical record of the patient with at least the dosage information (e.g., medication type, volume, delivery flow rate, delivery start time, delivery end time, prescribing healthcare practitioner, patient biometric data before, during, and after, the intravenous delivery, etc.).

FIG. 3 is intended to represent the major operations of an example method for regulating an intravenous injection using a wearable medical device. However, the operations depicted in FIG. 3 can comprise greater or lesser complexity than illustrated in FIG. 3, and they can happen, if they happen at all, in sequences other than what is necessarily shown in FIG. 3. As one example, operations 314 and 316 need not occur in all embodiments. For example, operations 314 and 316 do not occur in situations in which no adverse reaction is detected.

Figure 4:
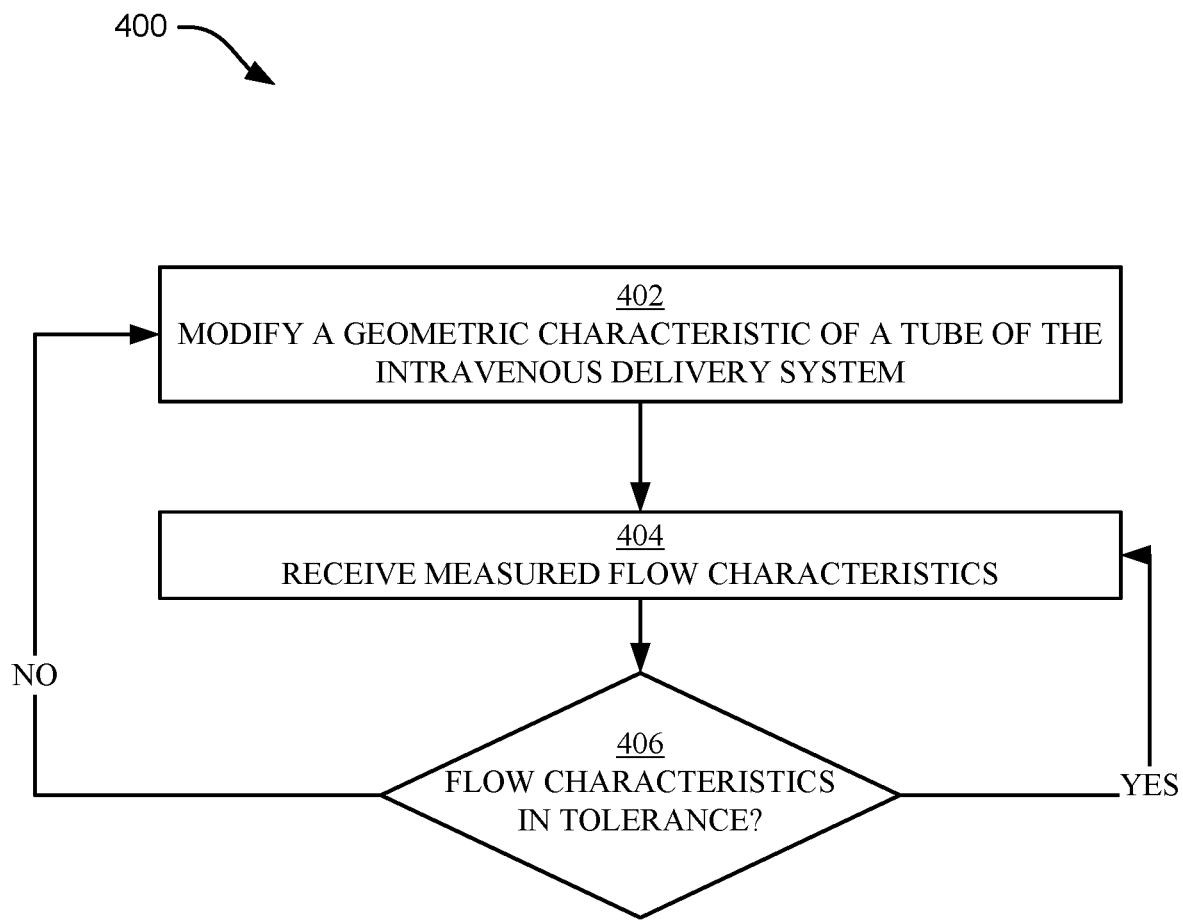
FIG. 4 illustrates a flowchart of an example method for regulating a flow rate of a volume of medication, in accordance with some embodiments of the present disclosure.

Referring now to FIG. 4, illustrated is a flowchart of an example method for regulating a flow rate of a medication, in accordance with some embodiments of the present disclosure. The method 400 can be implemented by a wearable medical device (e.g., wearable medical device 102 of FIG. 1, wearable medical device 200 of FIG. 2, or wearable medical device control unit 700 of FIG. 7). For clarity, the method 400 will be described as being executed by a wearable medical device control unit, however, the method 400 can also be implemented by alternative configurations of hardware and/or software.

In operation 402, the wearable medical device control unit can modify a geometric characteristic of a tube of an intravenous delivery system (e.g., intravenous delivery system 104 of FIG. 1). The geometric characteristic can be a curvature of the tube and/or a cross-sectional area of the tube.

For the purposes of the present disclosure, modifying the curvature of the tube can refer to bending, spiraling, twisting, or otherwise altering a curvature of the tube. The modified curvature can result in the tube having a curvature with conic, circular, elliptical, parabolic, hyperbolic, and/or other characteristics.

For the purposes of the present disclosure, modifying the cross-sectional area of the tube can refer to compressing, crimping, clamping, or otherwise modifying the tube such that the cross-sectional area of the tube and/or the shape of the cross-sectional area of the tube is altered.

Modifying the curvature and/or the cross-sectional area of the tube can alter flow characteristics (e.g., flow rate) of the medication. For example, altering a cross-sectional area of the tube can directly alter the flow rate by modifying the volume of the medication that can traverse the smallest cross-sectional area. As another example, altering the curvature of the tube can indirectly alter the flow rate by changing friction characteristics associated with the flow (e.g., laminar flow, turbulent flow, etc.). As another example, altering the curvature and/or cross-sectional area can indirectly alter the flow rate of the medication by altering the shear stress experienced by the fluid, thereby altering fluid viscosity and flow behavior for non-Newtonian fluids.

Non-Newtonian fluids can exhibit altered shear viscosity as a function of shear stress. For example, some fluids become less viscous with increased shear stress (e.g., thixotropic fluids, shear-thinning fluids). As another example, some fluids become more viscous with increased shear stress (e.g., dilatant fluids, shear thickening fluids). Fluids with lower viscosity can flow faster than fluids with higher viscosity. Aspects of the present disclosure can regulate flow rate by using changes in geometry to cause changes in shear stress which cause changes in fluid viscosity.

Thus, aspects of the present disclosure can control medication flow rate directly (e.g., as a result of cross-sectional areas) and indirectly (e.g., as a result of changed medication viscosity based on changed shear stress from the changes in geometry).

In operation 404, the wearable medical device control unit can receive measured flow characteristics. The wearable medical device control unit can receive measured flow characteristics directly or indirectly. Directly measured flow characteristics can use pressure measurements, dimension measurements, velocity measurements, flow rate measurements, or other measurements to directly estimate a flow rate (e.g., volumetric flow rate, mass flow rate, etc.) using components in the wearable medical device. Indirectly measured flow characteristics can be received by wireless communication with another device (e.g., a flow meter of the intravenous delivery system).

In operation 406, the wearable medical device control unit can determine if the measured flow characteristics are within an acceptable range (e.g., tolerance) of flow characteristics defined by the dosage information. If the wearable medical device control unit determines that the flow characteristics are within the acceptable range, then the method 400 can return to operation 404 and continue measuring (e.g., monitoring) the flow characteristics (e.g., at each time interval, approximately continuously, etc.). If the wearable medical device control unit determines that the flow characteristics are not in tolerance, the method 400 can return to operation 402 and modify the geometric characteristics of the tube.

In some embodiments, the wearable medical device control unit determines if the measured flow characteristics are within an acceptable range by calculating a difference between the measured flow characteristics and flow characteristics defined in the dosage information. If an absolute value of the difference is above a threshold, then the wearable medical device control unit can determine that the flow characteristics are not in tolerance in operation 406 and return to operation 402.

FIG. 4 is intended to represent the major operations of an example method for regulating a flow rate of a medication. However, the operations depicted in FIG. 4 can comprise greater or lesser complexity than illustrated in FIG. 4, and they can happen, if they happen at all, in sequences other than what is necessarily shown in FIG. 4.

Figure 5:
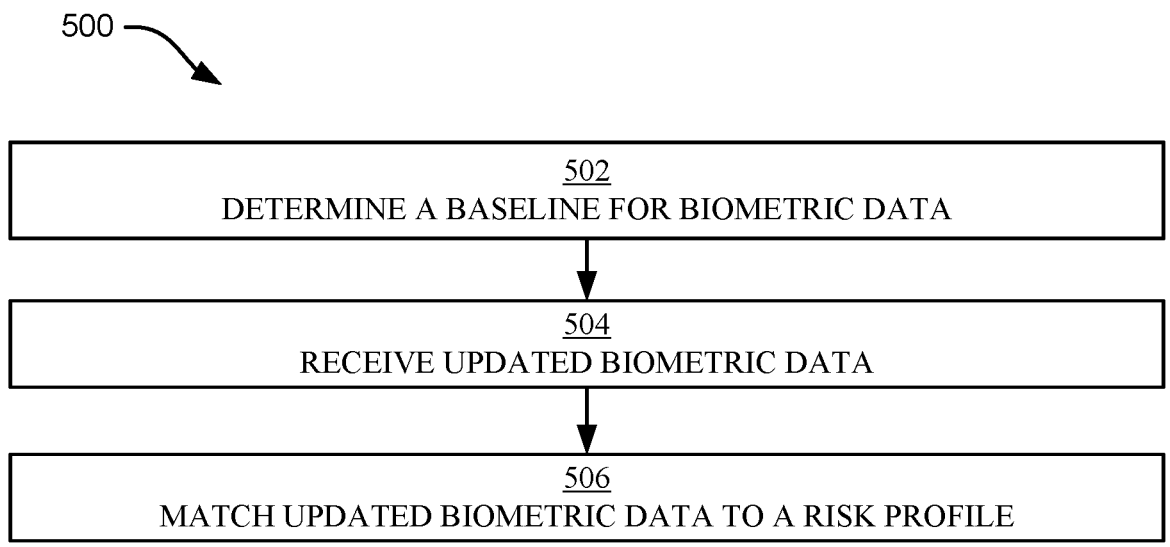
FIG. 5 illustrates a flowchart of an example method for detecting an adverse reaction to an intravenous injection, in accordance with some embodiments of the present disclosure.

Referring now to FIG. 5, illustrated is a flowchart of an example method for detecting an adverse reaction, in accordance with some embodiments of the present disclosure. The method 500 can be implemented by a wearable medical device (e.g., wearable medical device 102 of FIG. 1, wearable medical device 200 of FIG. 2, or wearable medical device control unit 700 of FIG. 7). For clarity, the method 500 will be described as being executed by a wearable medical device control unit, however, the method 500 can also be implemented by alternative configurations of hardware and/or software.

In operation 502, the wearable medical device control unit can determine a baseline for biometric data associated with the patient. The baseline can be retrieved from an electronic medical record associated with the patient (e.g., patient medical records 114 of FIG. 1) and/or from a time interval of sensor data collected by the one or more biometric sensors (e.g., biometric sensors 110 of FIG. 1 or biometric sensor 208 of FIG. 2).

In operation 504, the wearable medical device control unit can receive updated biometric data. In some embodiments, the updated biometric data is received during or after the delivery of the medication via the intravenous delivery system.

In operation 506, the wearable medical device control unit can match the updated biometric data to a risk profile. Matching the updated biometric data to a risk profile can mean, for respective types of biometric data in the updated biometric data, the updated biometric data falling within a range of values in the risk profile for the respective type of biometric data (e.g., meeting a criteria, satisfying a rule, etc.). For example, biometric data can include pulse rate, systolic blood pressure, and diastolic blood pressure. A risk profile can include a pulse rate above a first threshold, a systolic blood pressure below a second threshold, and any diastolic blood pressure. As another example, biometric data can include pulse rate, and a risk profile can comprise a pulse rate above a pulse rate threshold.

In some embodiments, operation 506 utilizes static rules with explicit numbers (e.g., a pulse rate above 90, a systolic blood pressure below 105). In other embodiments, operation 506 utilizes dynamic rules with relative numbers (e.g., a pulse rate 130% or higher of the baseline pulse rate, a systolic blood pressure of 80% or lower of the baseline systolic blood pressure).

FIG. 5 is intended to represent the major operations of an example method for detecting an adverse reaction. However, the operations depicted in FIG. 5 can comprise greater or lesser complexity than illustrated in FIG. 5, and they can happen, if they happen at all, in sequences other than what is illustrated in FIG. 5.

Figure 6:
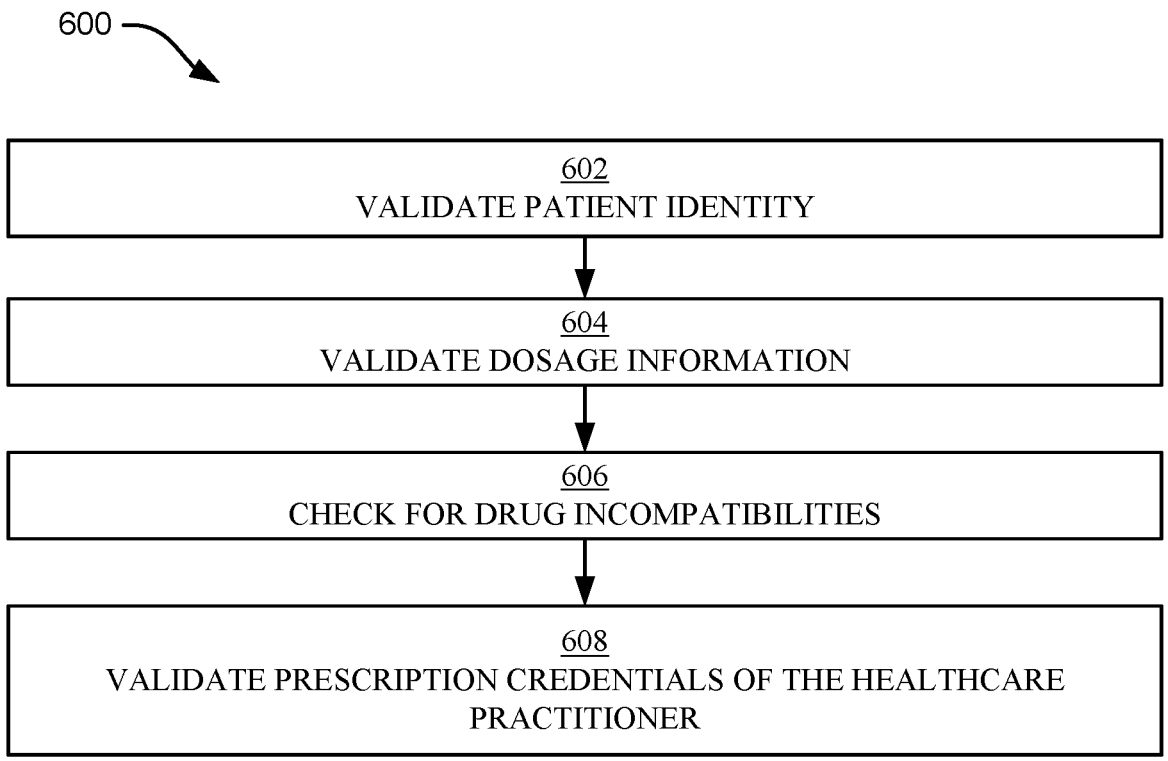
FIG. 6 illustrates a flowchart of an example method for verifying dosage information, in accordance with some embodiments of the present disclosure.

Referring now to FIG. 6, illustrated is a flowchart of an example method for verifying dosage information, in accordance with some embodiments of the present disclosure. The method 600 can be implemented by a wearable medical device (e.g., wearable medical device 102 of FIG. 1, wearable medical device 200 of FIG. 2, or wearable medical device control unit 700 of FIG. 7). For clarity, the method 600 will be described as being executed by wearable medical device control unit, however, the method 600 can also be implemented by alternative configurations of hardware and/or software. In some embodiments, the method 600 is a sub-method of operation 308 of FIG. 3.

In operation 602, the wearable medical device control unit can validate a patient identity. Validating a patient identity can comprise determining a patient identity associated with the dosage is the same as (e.g., matching, identical to, consistent with, etc.) a patient identity of an electronic medical record associated with the wearable medical device.

In operation 604, the wearable medical device control unit can validate dosage information. Validating dosage information can comprise determining that a volume and flow rate of the dosage information are within predefined guidelines. In some embodiments, operation 604 retrieves predefined guidelines from a medical database (e.g., medical database 112 of FIG. 1).

In operation 606, the wearable medical device control unit can check for drug incompatibilities. Checking for drug incompatibilities can comprise identifying any medications the patient is currently prescribed (e.g., by querying an electronic medical record such as patient medical records 114 of FIG. 1), and determining if any of the prescribed medications are incompatible with the medication to be delivered intravenously. In some embodiments, operation 606 comprises querying a medical database (e.g., medical database 112 of FIG. 1) to determine if any medications currently prescribed to the patient are incompatible with the medication to be delivered intravenously.

In operation 608, the wearable medical device control unit can validate the credentials of the healthcare practitioner prescribing the medication. For example, different types of medications may require different levels of authority to authorize prescriptions of those medications. The authority requirements can be stored in a medical database (e.g., medical database 118 of FIG. 1) and authority levels of individual users can be indicated in a user profile used to access a user console (e.g., user console 106 of FIG. 1)

FIG. 6 is intended to represent the major operations of an example method for detecting an adverse reaction. However, the operations depicted in FIG. 6 can comprise greater or lesser complexity than illustrated in FIG. 6, and they can happen, if they happen at all, in sequences other than what is illustrated in FIG. 6.

Figure 7:
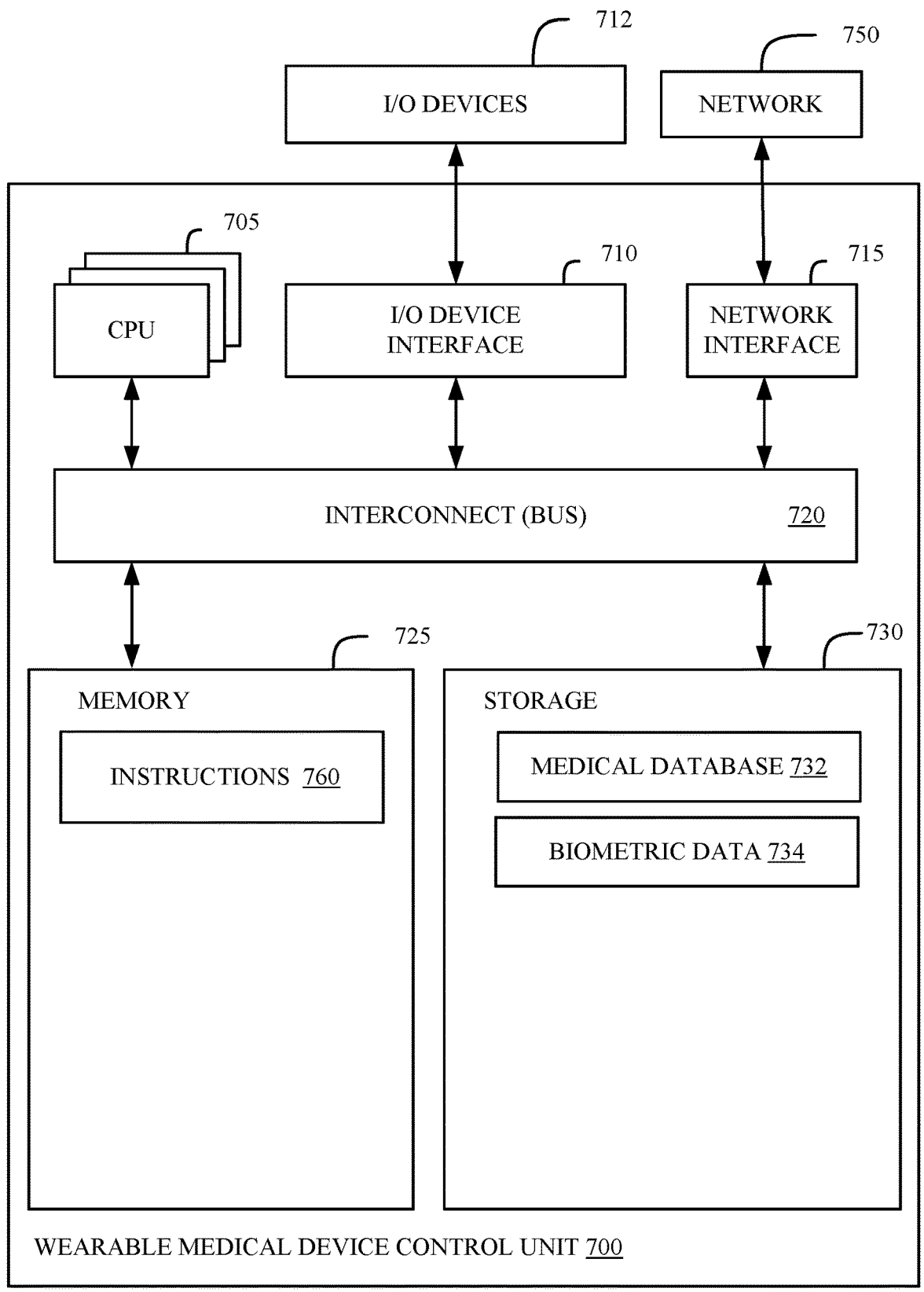
FIG. 7 illustrates a block diagram of an example wearable medical device control unit, in accordance with some embodiments of the present disclosure.

FIG. 7 illustrates a block diagram of an example wearable medical device control unit 700 in accordance with some embodiments of the present disclosure. In some embodiments, the wearable medical device control unit 700 can be consistent with wearable medical device 102 of FIG. 1 and/or wearable medical device 200 of FIG. 2. In various embodiments, wearable medical device control unit 700 performs any of the methods described in FIGS. 3-6. In some embodiments, wearable medical device control unit 700 provides instructions for one or more of the methods described in FIGS. 3-6 to a client machine such that the client machine executes the method, or a portion of the method, based on the instructions provided by the wearable medical device control unit 700.

The wearable medical device control unit 700 includes a memory 725, storage 730, an interconnect (e.g., BUS) 720, one or more CPUs 705 (also referred to as processors 705 herein), an I/O device interface 710, I/O devices 712, and a network interface 715.

Each CPU 705 retrieves and executes programming instructions stored in the memory 725 or storage 730. The interconnect 720 is used to move data, such as programming instructions, between the CPUs 705, I/O device interface 710, storage 730, network interface 715, and memory 725. The interconnect 720 can be implemented using one or more busses. The CPUs 705 can be a single CPU, multiple CPUs, or a single CPU having multiple processing cores in various embodiments. In some embodiments, a CPU 705 can be a digital signal processor (DSP). In some embodiments, CPU 705 includes one or more 3D integrated circuits (3DICs) (e.g., 3D wafer-level packaging (3DWLP), 3D interposer based integration, 3D stacked ICs (3D-SICs), monolithic 3D ICs, 3D heterogeneous integration, 3D system in package (3DSiP), and/or package on package (PoP) CPU configurations). Memory 725 is generally included to be representative of a random access memory (e.g., static random access memory (SRAM), dynamic random access memory (DRAM), or Flash). The storage 730 is generally included to be representative of a non-volatile memory, such as a hard disk drive, solid state device (SSD), removable memory cards, optical storage, or flash memory devices. In an alternative embodiment, the storage 730 can be replaced by storage area-network (SAN) devices, the cloud, or other devices connected to the wearable medical device control unit 700 via the I/O devices interface 710 or a network 750 via the network interface 715.

In some embodiments, the memory 725 stores instructions 760 and the storage 730 stores medical database 732 and biometric data 734. However, in various embodiments, the instructions 760, the medical database 732, and the biometric data 734 are stored partially in memory 725 and partially in storage 730, or they are stored entirely in memory 725 or entirely in storage 730, or they are accessed over a network 750 via the network interface 715.

The medical database 732 can be consistent with medical database 112 of FIG. 1. Medical database 732 can store electronic medical records, medication information (e.g., dosage volumes, dosage flow rates, medication incompatibilities, etc.), and risk profiles (e.g., biometric data indicating an adverse reaction to a medication, a medical emergency, etc.). Biometric data 734 can store data collected from at least one biometric sensor physically attached to, or communicatively coupled to, the wearable medical device.

The instructions 760 are processor executable instructions for executing any portion of, any combination of, or all of the methods previously discussed in FIGS. 3-6.

In various embodiments, the I/O devices 712 include an interface capable of presenting information and receiving input. For example, I/O devices 712 can present information to a user interacting with wearable medical device control unit 700 and receive input from the user.

Wearable medical device control unit 700 is connected to the network 750 via the network interface 715. Network 750 can comprise a physical, wireless, cellular, or different network. In some embodiments, network 750 is consistent with network 120 of FIG. 1.

FIG. 7 is intended to represent the major components of an example wearable medical device control unit 700 according to embodiments of the present disclosure. In some embodiments, however, individual components can have greater or lesser complexity than shown in FIG. 7, and components other than, or in addition to those shown in FIG. 7 can be present. Furthermore, in some embodiments, various components illustrated in FIG. 7 can have greater, lesser, or different functionality than shown in FIG. 7.

Embodiments of the present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or subset of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

While it is understood that the process software (e.g., any of the instructions stored in instructions 760 of FIG. 7 and/or any software configured to perform any subset of the methods described with respect to FIGS. 3-6) may be deployed by manually loading it directly in the client, server, and proxy computers via loading a storage medium such as a CD, DVD, etc., the process software may also be automatically or semi-automatically deployed into a computer system by sending the process software to a central server or a group of central servers. The process software is then downloaded into the client computers that will execute the process software. Alternatively, the process software is sent directly to the client system via e-mail. The process software is then either detached to a directory or loaded into a directory by executing a set of program instructions that detaches the process software into a directory. Another alternative is to send the process software directly to a directory on the client computer hard drive. When there are proxy servers, the process will select the proxy server code, determine on which computers to place the proxy servers' code, transmit the proxy server code, and then install the proxy server code on the proxy computer. The process software will be transmitted to the proxy server, and then it will be stored on the proxy server.

Embodiments of the present invention may also be delivered as part of a service engagement with a client corporation, nonprofit organization, government entity, internal organizational structure, or the like. These embodiments may include configuring a computer system to perform, and deploying software, hardware, and web services that implement, some or all of the methods described herein. These embodiments may also include analyzing the client's operations, creating recommendations responsive to the analysis, building systems that implement subsets of the recommendations, integrating the systems into existing processes and infrastructure, metering use of the systems, allocating expenses to users of the systems, and billing, invoicing (e.g., generating an invoice), or otherwise receiving payment for use of the systems.

What is claimed is:

1. A wearable medical device comprising:
   an annular housing configured to attach to a wrist of a patient;
   a first receptacle attached to the annular housing for receiving a first portion of a tube of an intravenous delivery system, wherein the first portion of the tube comprises a shape-memory polymer;
   a flow regulator attached to the annular housing and in contact with the first portion of the tube, wherein the flow regulator is configured to modify a geometric characteristic of the first portion of the tube by activating the shape-memory polymer, wherein activating the shape-memory polymer alters a curvature of the tube, wherein altering the curvature of the tube alters a flow of a medication in the tube;
   a pulse monitor attached to the annular housing and configured to contact the wrist of the patient and measure a pulse of the patient; and
   a wireless transmitter for communicating with a user console.

2. The wearable medical device according to claim 1, further comprising:
   a control unit comprising a processor and storing programmable logic executable by the processor to cause the processor to:
      receive, at the wireless transmitter and from the user console, a dosage, wherein the dosage comprises a drug type, a dosage flow rate, and a volume;
      receive, at the wireless transmitter and from a flow meter communicatively coupled to the wearable medical device, a first flow rate, wherein the first flow rate measures a flow rate in the first portion of the tube;
      compare the first flow rate to the dosage flow rate;
      determine that a difference between the first flow rate and the dosage flow rate is above a threshold; and
      modify the flow regulator to alter the geometric characteristic of the tube.

3. The wearable medical device according to claim 2, wherein the control unit is further configured to:
   receive biometric data from the pulse monitor;
   detect a patient condition based on the biometric data; and
   send an alert to the user console indicating the patient condition.

4. The wearable medical device according to claim 1, wherein at least a portion of the annular housing comprises an elastomer having an elastic modulus less than 1.0 gigapascals (GPa).

5. The wearable medical device according to claim 1, wherein the annular housing comprises a first hinge and a first fixing mechanism.

6. The wearable medical device according to claim 5, wherein the first fixing mechanism comprises a magnetic fixing mechanism.

7. The wearable medical device according to claim 5, wherein the first fixing mechanism comprises a mechanical fixing mechanism.

8. The wearable medical device according to claim 1, wherein the flow is altered by a shear stress applied to the medication in the tube at the curvature.

9. The wearable medical device according to claim 1, wherein altering the curvature of the tube is selected from a group consisting of: bending the tube, spiraling the tube, and twisting the tube.

10. A wearable medical device comprising:
   an annular housing configured to attach to a wrist of a patient;
   a first receptacle attached to the annular housing for receiving a first portion of a tube of an intravenous delivery system, wherein the first portion of the tube comprises a shape-memory polymer;
   a flow regulator attached to the annular housing and in contact with the first portion of the tube, wherein the flow regulator is configured to alter a shear stress of a medication in the tube by activating the shape-memory polymer;
   a pulse monitor attached to the annular housing and configured to contact the wrist of the patient and measure a pulse of the patient; and
   a wireless transmitter for communicating with a user console.

11. The wearable medical device according to claim 10, further comprising:
   a control unit comprising a processor and storing programmable logic executable by the processor to cause the processor to:
      receive, at the wireless transmitter and from the user console, a dosage, wherein the dosage comprises a drug type, a dosage flow rate, and a volume;
      receive, at the wireless transmitter and from a flow meter communicatively coupled to the wearable medical device, a first flow rate, wherein the first flow rate measures a flow rate in the first portion of the tube;
      compare the first flow rate to the dosage flow rate;
      determine that a difference between the first flow rate and the dosage flow rate is above a threshold; and
      modify the flow regulator to alter the shear stress of the medication in the tube.

12. The wearable medical device according to claim 11, wherein the control unit is further configured to:
   receive biometric data from the pulse monitor;
   detect a patient condition based on the biometric data; and
   send an alert to the user console indicating the patient condition.

13. The wearable medical device according to claim 1, wherein the flow is altered by altered friction characteristics of the flow of the medication in the tube at the curvature.

* * * * *